(12) United States Patent
MacAdam et al.

(10) Patent No.: US 8,945,116 B2
(45) Date of Patent: Feb. 3, 2015

(54) MAPPING AND ABLATION METHOD FOR THE TREATMENT OF VENTRICULAR TACHYCARDIA

(75) Inventors: David MacAdam, Millbury, MA (US); Ding Sheng He, Tyngsboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2490 days.

(21) Appl. No.: 11/597,082

(22) PCT Filed: May 17, 2005

(86) PCT No.: PCT/US2005/017081
§ 371 (c)(1),
(2), (4) Date: Jul. 16, 2008

(87) PCT Pub. No.: WO2005/115226
PCT Pub. Date: Dec. 8, 2005

(65) Prior Publication Data
US 2008/0281391 A1 Nov. 13, 2008

Related U.S. Application Data

(60) Provisional application No. 60/571,781, filed on May 17, 2004, provisional application No. 60/571,843, filed on May 17, 2004, provisional application No. 60/571,821, filed on May 17, 2004.

(51) Int. Cl.
*A61B 18/12* (2006.01)
*A61B 5/042* (2006.01)
(Continued)

(52) U.S. Cl.
CPC .............. *A61B 18/1492* (2013.01); *A61B 5/042* (2013.01); *A61B 2018/00214* (2013.01); *A61B 2018/00839* (2013.01)
USPC ................ 606/41; 606/34; 128/898; 607/101

(58) Field of Classification Search
USPC ........... 606/24, 27–28, 32, 34, 38, 41, 47–50; 607/101–102, 122
See application file for complete search history.

(56) References Cited

U.S. PATENT DOCUMENTS

| 5,311,866 A | 5/1994 | Kagan et al. |
| 5,397,341 A * | 3/1995 | Hirschberg et al. ........... 607/122 |
| 5,476,495 A * | 12/1995 | Kordis et al. ................. 607/122 |
| 5,549,108 A | 8/1996 | Edwards et al. |
| 5,814,027 A * | 9/1998 | Hassett et al. ................ 604/528 |

(Continued)

FOREIGN PATENT DOCUMENTS

| WO | WO-99/05971 A | 2/1999 |
| WO | WO 2005/008418 A2 | 1/2005 |

OTHER PUBLICATIONS

International Preliminary Report on Patentability from PCT/US2005/017080 dated Nov. 21, 2006.

(Continued)

*Primary Examiner* — Michael Peffley
*Assistant Examiner* — Khadijeh Vahdat
(74) *Attorney, Agent, or Firm* — Seager, Tufte & Wickhem, LLC

(57) ABSTRACT

An apparatus for mapping and/or ablating tissue includes a braided conductive member that may be inverted to provide a ring-shaped surface. When a distal tip of the braided conductive member is retracted within the braided conductive member, the lack of a protrusion allows the ring-shaped surface to contact a tissue wall such as a cardiac wall. In an alternative configuration, the braided conductive member may be configured with the distal portion forming a proboscis that can be used to stably position the braided conductive member relative to a blood vessel, such as a ventricular outflow tract. The braided conductive member has a plurality of electronically active sites that may be accessed individually for stable mapping over a broad area for stable mapping or ablation to form broad and deep lesions.

15 Claims, 10 Drawing Sheets

(51) Int. Cl.
*A61B 18/14* (2006.01)
*A61B 18/00* (2006.01)

(56) References Cited

U.S. PATENT DOCUMENTS

| | | | |
|---|---|---|---|
| 6,014,581 A | 1/2000 | Whayne et al. | |
| 6,240,307 B1 | 5/2001 | Beatty et al. | |
| 6,292,702 B1 | 9/2001 | King et al. | |
| 6,315,778 B1 | 11/2001 | Gambale et al. | |
| 6,471,699 B1 * | 10/2002 | Fleischman et al. | 606/41 |
| 6,837,886 B2 | 1/2005 | Collins et al. | |
| 2001/0025175 A1 * | 9/2001 | Panescu et al. | 606/41 |
| 2001/0044585 A1 * | 11/2001 | Dupree et al. | 600/509 |
| 2001/0047129 A1 * | 11/2001 | Hall et al. | 600/374 |
| 2002/0062124 A1 * | 5/2002 | Keane | 606/41 |
| 2002/0065459 A1 | 5/2002 | MacAdam et al. | |
| 2002/0091330 A1 | 7/2002 | MacAdam et al. | |
| 2002/0107511 A1 * | 8/2002 | Collins et al. | 606/41 |
| 2002/0165535 A1 * | 11/2002 | Lesh et al. | 606/41 |
| 2002/0183638 A1 | 12/2002 | Swanson | |
| 2003/0065318 A1 * | 4/2003 | Pendekanti | 606/41 |
| 2004/0093016 A1 * | 5/2004 | Root et al. | 606/200 |

OTHER PUBLICATIONS

Supplementary Partial European Search Report from EP05749957 dated Jun. 24, 2009.

Miller et al., "Catheter Ablation of Ventricular Tachycardia in Patients with Structural Heart Disease," Cardiology in Review, vol. 9, No. 6, 2001, pp. 302-311.

Delacrétaz et al., "Catheter Ablation of Ventricular Tachycardia in Patients with Coronary Heart Disease, Part II: Clinical Aspects, Limitations, and Recent Developments," Journal of Pacing and Clinical Electrophysiology, vol. 24, Sep. 2001, Part I, pp. 1403-1411.

Stevenson et al., "Strategies for Catheter Ablation of Scar-Related Ventricular Tachycardia," Current Cardiology Reports, 2000, 2:537-544.

Varma et al., "Therapy of "Idiopathic" Ventricular Tachycardia," Journal of Cardiovascular Electrophysiology, vol. 8, Jan. 1997, pp. 104-116.

Wolf et al., "Sudden Death Following Rupture of a Right Ventricular Aneurysm 9 Months after Ablation Therapy of the Right Ventricular Outflow Tract," Journal of Pacing and Clinical Electrophysiology, vol. 25, No. 7, Jul. 2002, 1135-1137.

Stevenson et al., "Overview of VT Ablation," downloaded from http://www.medscape.com/viewarticle/443348, downloaded on Apr. 15, 2005, pp. 1-5.

Belhassen et al., "Idiopathic Ventricular Tachycardia and Fibrillation," Journal of Cardiovascular Electrophysiology, vol. 4, No. 3, Jun. 1993.

Eurospace Supplements, vol. 3, Jul. 2002, p. A144, pp. 17-20.

International Search Report from PCT/US05/017081 dated May 22, 2007.

* cited by examiner

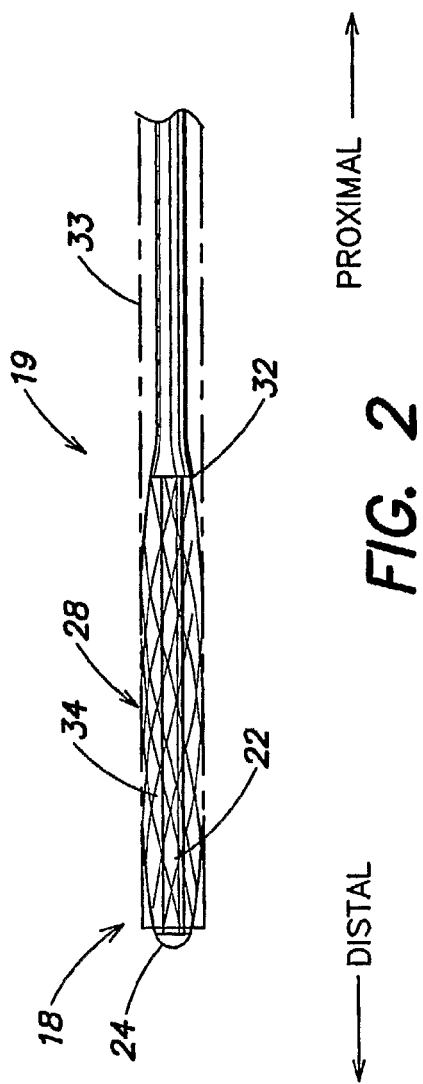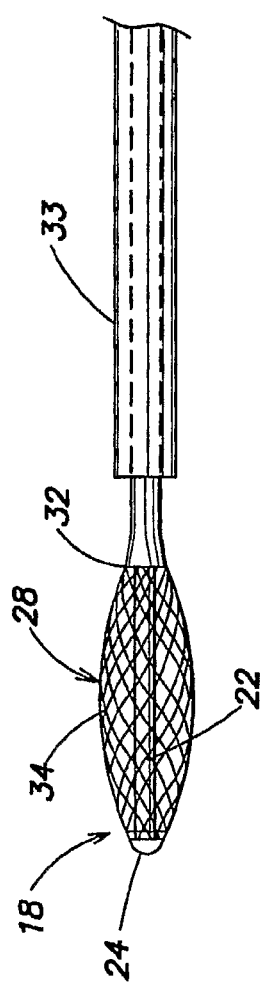

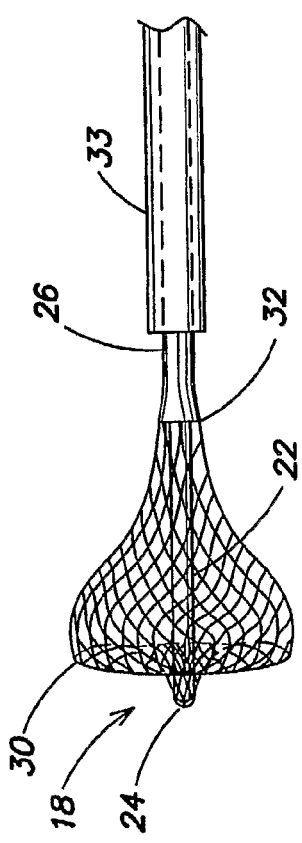
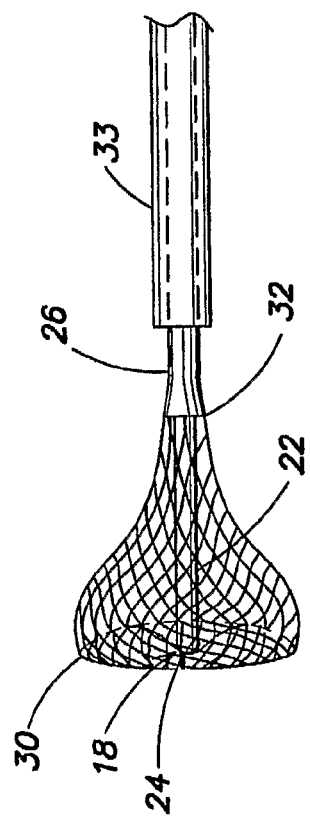

MAPPING AND ABLATION METHOD FOR THE TREATMENT OF VENTRICULAR TACHYCARDIA

RELATED APPLICATIONS

This application claims priority under 35 U.S.C. §119(e) to U.S. Provisional Application Ser. No. 60/571,781, entitled "MAPPING AND ABLATION METHOD AND APPARATUS FOR THE TREATMENT OF IDIOPATHIC VENTRICULAR TACHYCARDIA ORIGINATING FROM RVOT OR LVOT," filed on May 17, 2004, which is herein incorporated by reference in its entirety, and U.S. Provisional Application Ser. No. 60/571,843, entitled "MAPPING AND ABLATION METHOD AND APPARATUS FOR THE TREATMENT OF IDIOPATHIC VENTRICULAR TACHYCARDIA," filed on May 17, 2004, which is herein incorporated by reference in its entirety. This application claims priority under 35 U.S.C. §119(e) to U.S. Provisional Application Ser. No. 60/571,821, entitled "METHOD AND APPARATUS FOR MAPPING AND/OR ABLATION OF CARDIAC TISSUE," filed on May 17, 2004, which is herein incorporated by reference in its entirety.

BACKGROUND OF INVENTION

1. Field of Invention

The invention relates generally to medical devices for performing mapping and ablation procedures. More particularly, the invention relates to a system for mapping and/or ablating cardiac walls.

2. Discussion of Related Art

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

Over time, the electrical impulses traveling through the heart can begin to travel in improper directions, thereby causing the heart chambers to contract at improper times. Such a condition is generally termed a cardiac arrhythmia, and can take many different forms. When the chambers contract at improper times, the amount of blood pumped by the heart decreases, which can result in premature death of the person.

Techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping may be active or passive. Active mapping, sometimes called "pace mapping," typically involves percutaneously introducing a catheter having one or more electrodes into the patient, passing the catheter through a blood vessel (e.g. the femoral vein or artery) and into an endocardial site (e.g., the atrium or ventricle of the heart), and deliberately inducing an arrhythmia so that a continuous, simultaneous recording can be made with a multichannel recorder at each of several different endocardial positions. Passive mapping techniques typically involve sensing electrical signals from the electrodes on the catheter.

When an arrythromogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrythromogenic focus. Ablation is carried out by applying energy to the catheter electrodes. The ablation energy can be, for example, RF, DC, ultrasound, microwave, or laser radiation.

Atrial fibrillation together with atrial flutter are the most common sustained arrhythmias found in clinical practice. Current understanding is that atrial fibrillation is frequently initiated by a focal trigger from the orifice of or within one of the pulmonary veins. Though mapping and ablation of these triggers appears to be curative in patients with paroxysmal atrial fibrillation, there are a number of limitations to ablating focal triggers via mapping and ablating the earliest site of activation with a "point" radiofrequency lesion. One way to circumvent these limitations is to determine precisely the point of earliest activation. Once the point of earliest activation is identified, a lesion can be generated to electrically isolate the trigger with a lesion; firing from within those veins would then be eliminated or unable to reach the body of the atrium, and thus could not trigger atrial fibrillation.

Another method to treat focal arrhythmias is to create a continuous, annular lesion around the ostia (i.e., the openings) of either the veins or the arteries leading to or from the atria, thus "corralling" the signals emanating from any points distal to the annular lesion. Conventional techniques include applying multiple point sources around the ostia in an effort to create such a continuous lesion. Such a technique is relatively involved, and requires significant skill and attention from the clinician performing the procedures.

Another source of arrhythmias may be from reentrant circuits in the myocardium itself. Such circuits may not necessarily be associated with vessel ostia, but may be interrupted by means of ablating tissue either within the circuit or circumscribing the region of the circuit. It should be noted that a complete "fence" around a circuit or tissue region is not always required in order to block the propagation of the arrhythmia; in many cases simply increasing the propagation path length for a signal may be sufficient. Conventional means for establishing such lesion "fences" include a multiplicity of point-by-point lesions, dragging a single electrode across tissue while delivering energy, or creating an enormous lesion intended to inactivate a substantive volume of myocardial tissue.

U.S. Pat. No. 6,315,778 B1, entitled "Apparatus For Creating A Continuous Annular Lesion," which is herein incorporated by reference, discloses a medical device which is capable of ablating a ring of tissue around the ostia of either veins or arteries leading to or from the atria. The medical device includes a protrusion that inserts into an ostium, thereby allowing electrodes to contact tissue near the ostium.

In some instances, it is desirable to perform mapping and/or ablation procedures on a cardiac wall (or other tissue) that is not located near an ostium. In such a scenario, the lack of a protrusion may help to allow electrodes of a device contact the cardiac wall or other tissue. In other cases, mapping and/or ablation may be desired at several locations around an ostium and it would be helpful to be able to position electrodes without concern for a protrusion that may hinder contact between electrodes and the cardiac wall.

Another type of arrhythmia is Ventricular tachycardia. Ventricular tachycardia (VT) usually arises in diseased myocardium. However, VT can occur in the absence of structural heart disease, or at least in hearts in which current diagnostic techniques fail to identify any anatomic or functional abnormalities. These arrhythmias have been termed "idiopathic VTs". The mechanisms underlying idiopathic VT are varied and include reentry and triggered activity due to delayed after depolarizations.

Idiopathic VTs that arise from the right or left ventricular outflow tract (RVOT VT and LVOT VT) have been reported. Thus RVOT VT and LVOT VT patients could be treated with RF ablation. However, the success rate of ablation therapy for treatment of VT is affected by many factors, such as the inability to induce tachycardia to permit mapping, and the presence of deep, often septal sites of origin that are resistant to RF ablation with conventional ablation catheters, usually a 4-mm ablation catheter. Treating VT in the area of the outflow track with ablation therapy has been difficult.

SUMMARY OF INVENTION

Embodiments of the present invention encompass apparatus and methods for mapping electrical activity within the heart. Embodiments of the present invention also encompass methods and apparatus for creating lesions in the heart tissue (ablating) to create a region of necrotic tissue which serves to disable the propagation of errant electrical impulses caused by an arrhythmia. The apparatus and methods described herein also may be used for mapping and ablating of tissue other than heart tissue.

In one aspect, the invention relates to a method of treating an arrhythmia in a heart, comprising the acts of: introducing a substrate into a chamber of the heart; placing the substrate in contact with the heart while in a first configuration; (c) performing mapping and/or pacing by transmitting electrical signals between the substrate and a control location; reconfiguring the substrate into a second configuration, different than the first configuration; and ablating a region of the heart adjacent the substrate.

In another aspect, the invention relates to a method of detecting a focus of an arrhythmia in a heart, comprising the acts of introducing into a chamber of the heart a substrate having a plurality of electrically active sites thereon, the substrate configured to have a distally facing surface with a first area; reconfiguring the substrate to expand the distally facing surface to have a second area, larger than the first area; contacting the distally facing surface with the heart in a region having the second surface area; using the electrically active sites to detect at least one focus of the arrhythmia over the region of the heart; and ablating a sub-region of the region selected in response to the detection of a focus within the region.

In a further aspect, the invention relates to a method of detecting a focus of an arrhythmia in a heart, comprising the acts of introducing a catheter having a substrate into a chamber of the heart; configuring the substrate to provide a surface; positioning the catheter so that a plurality of electrically active sites on the surface are in electrical contact with the endocardium; and using signals transmitted between a control location and the plurality of electrically active sites to detect a focus.

In yet a further aspect, the invention relates to A method of treating an arrhythmia in a heart, comprising the acts of introducing a catheter having a plurality of electrically active sites into the heart; with the catheter, sensing electrical signals produced by the heart; with the catheter, providing electrical stimulus to the heart; and with the catheter, ablating a region of the heart.

In a further aspect, the invention relates to A method of treating ventricular tachycardia in a heart, comprising the acts of positioning a surface of a catheter against a surface of the heart adjacent the ostium of an outflow tract of a ventricle of the heart, the surface of the catheter having a periphery substantially the same as or greater than a periphery of the ostium; using the catheter to detect a position of at least one focus of the ventricular tachycardia; and selectively ablating a portion of the heart based on the position of the at least one focus.

BRIEF DESCRIPTION OF DRAWINGS

The accompanying drawings are not intended to be drawn to scale. In the drawings, like components that are illustrated in various figures are represented by a like numeral. For purposes of clarity, not every component may be labeled in every drawing. In the drawings:

FIG. 2 illustrates a braided conductive member in an undeployed state that may be used in one embodiment of the invention;

FIG. 3 illustrates a braided conductive member in a partially expanded state that may be used in one embodiment of the invention;

FIG. 4 illustrates a braided conductive member in an inverted state that may be used in one embodiment of the invention;

FIG. 5 illustrates a braided conductive member in an inverted state where a distal end of the braided conductive member does not protrude distally from the inverted braided conductive member that may be used in one embodiment of the invention;

DETAILED DESCRIPTION

Figure 1:
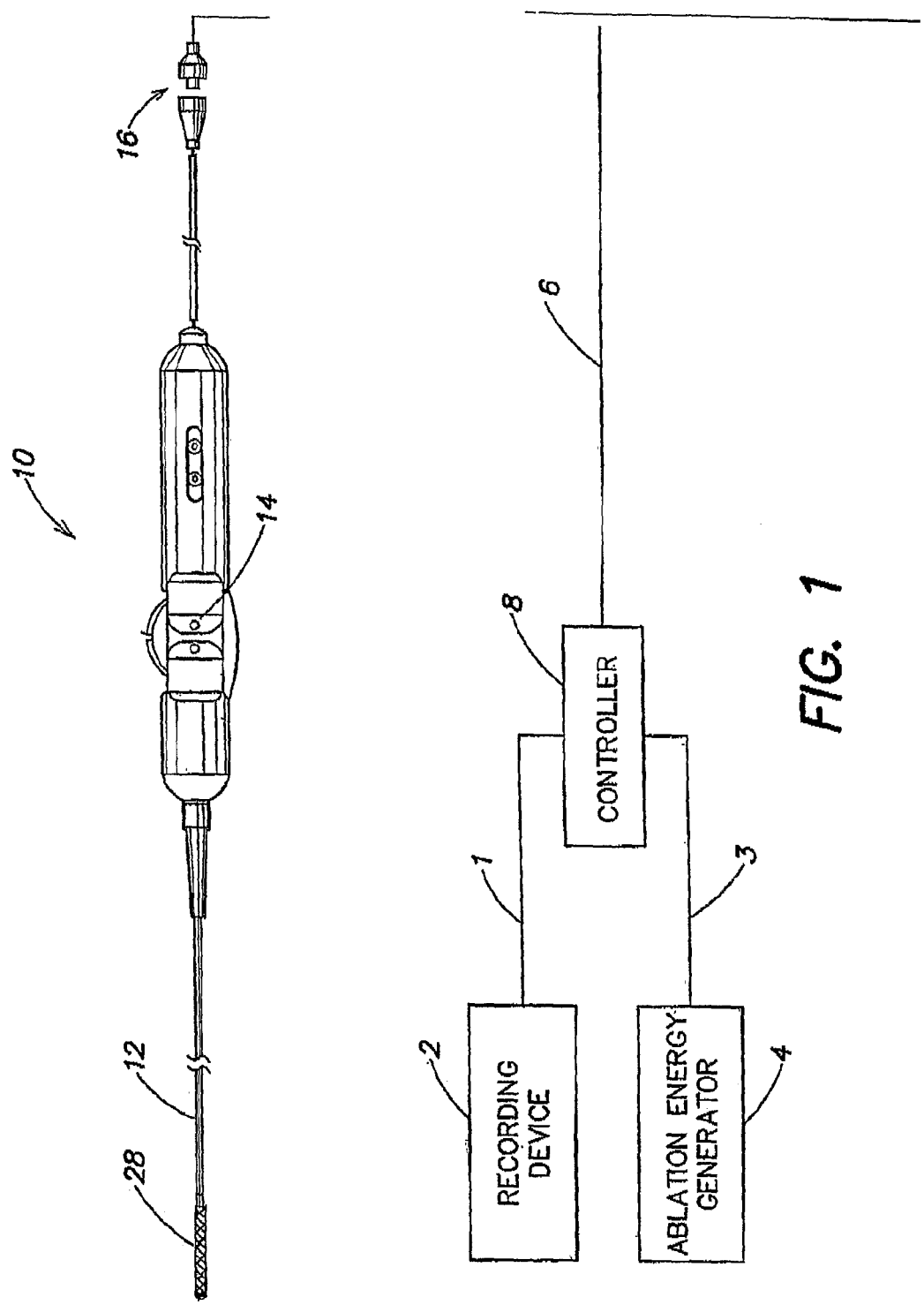
FIG. 1 illustrates an overview of a mapping and ablation catheter system that may be used in one embodiment of the present invention.

This invention is not limited in its application to the details of construction and the arrangement of components and acts set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

System Overview

Reference is now made to FIG. 1, which illustrates an overview of a electrophysiology system, such as may be used for mapping and/or ablation to detect or treat cardiac arrhythmia. The system includes a catheter 10 having a shaft portion 12, a control handle 14, a connector portion 16, and a braided conductive member 28. A controller 8 is connected to connector portion 16 via cable 6. Ablation energy generator 4 may be connected to controller 8 via cable 3. A recording device 2 may be connected to controller 8 via cable 1. When used in an ablation application, controller 8 is used to control ablation energy provided to catheter 10 by ablation energy generator 4. When used in a mapping application, controller 8 is used to process signals coming from catheter 10 and to provide these signals to recording device 2. Although illustrated as separate devices, recording device 2, ablation energy generator 4, and controller 8 could be incorporated into a single device or two devices.

In this description, various aspects and features of exemplary embodiments of the present invention will be described. These aspects and features are discussed separately for clarity. One skilled in the art will appreciate that the features may be selectively combined in a device depending upon the particular application. Furthermore, any of the various features may be incorporated in a catheter and associated method of use for either mapping and/or ablation procedures.

Catheter Overview

Reference is now made to FIGS. 2-5, which illustrate a catheter that may be used in the electrophysiology system of FIG. 1. Embodiments of the present invention generally include a catheter and methods of its use for mapping and ablation in electrophysiology procedures. FIG. 2 illustrates braided conductive member 28 in an unexpanded state. In this embodiment, the unexpanded state of the braided conductive member is an undeployed configuration. Braided conductive member 28 is, in one embodiment of the invention, a plurality of interlaced, electrically conductive filaments 34 which are attached at a distal end 18 with a cap 24 and also at a proximal end 19 with an anchoring element 32. Of course any suitable element or method may be used to attach or anchor filaments 34.

FIG. 3 illustrates braided conductive member 28 in a partially expanded state. Each of FIGS. 2 and 3 show a state in which braided conductive member 28 is completely everted. FIG. 4 illustrates braided conductive member 28 in a first deployed configuration option which may be used to locate braided conductive member 28 at an ostium.

In FIG. 4, distal end 18 of braided conductive member 28 is partially inverted. The terms "partially invert" and "partially inverted", for purposes herein, refer to a configuration in which portions of filaments are retracted within the braided conductive member such that they are at least partially surrounded by other portions of filaments. A tip, or other portions of the braided conductive member may protrude distally from any distally-facing surface of the braided conductive member when the braided conductive member is partially inverted.

FIG. 5 illustrates braided conductive member 28 in a second deployed configuration option which may be used to effect contact between an annular surface of braided conductive member 28 and a cardiac wall (see, for example, FIG. 11) other cardiac tissue, or other target tissue. In FIG. 5, the distal tip of braided conductive member 28 is inverted. The terms "invert" or "inverted", for purposes herein, refer to a configuration in which the distal tip or distal end of the braided conductive member is retracted such that the distal tip does not protrude distally from a distally-facing surface of the braided conductive member. For purposes herein, the terms "evert" or "everted" refer to a configuration in which the distal tip or distal end of the braided conductive member protrudes distally from any distally-facing annular surface that is present. An everted configuration does not, however, require that a distally-facing annular surface be present. In some embodiments, such as the embodiment illustrated in FIG. 2, the braided conductive member is fully elongated in an everted configuration. The term "completely everted", when referring to a distal region of a braided conductive member, refers to a configuration in which no portion of the distal region of the braided conductive member is inverted within itself.

A braided conductive member adjustment element, such as a cable 22, is attached to distal end 18 of braided conductive member 28. Cable 22 may extend through a lumen (not shown) in shaft portion 12 and through the interior of braided conductive member 28. Cable 22 may be attached to distal end 18 of braided conductive member 28 using cap 24, an anchor band, or any suitable attachments or anchoring element or method known in the art. At the control handle end, cable 22 may be attached to a control element, such as a slide actuator for example, that allows a user to retract and advance cable 22. It should be noted that cable 22 is a separate element from cables 1, 3 and 6. Of course, braided conductive member adjustment element need not be a cable as any suitable element for adjusting the braided conductive member may be used. For example, a sheath may be used to push the braided conductive member over the distal tip of the braided conductive member to invert braided conductive member 28.

In operation, moving cable 22 in the proximal direction causes braided conductive member 28 to compress longitudinally and/or to expand radially, as shown in FIG. 3. Further proximal movement of cable 22 causes a portion of braided conductive member 28 to invert as shown in FIG. 4. Even further proximal movement of cable 22 may retract distal end 18 such that distal end 18 is encircled by a portion of braided conductive member 28. In some embodiments, distal end 18 may be surrounded or partially surrounded by a portion of braided conductive member 28 that does not form a circle.

In some embodiments, a certain amount of movement of cable 22 in the proximal direction may occur without user actuation due to the bias of the braided conductive member 28. For example, braided conductive member 28 may be longitudinally extended beyond a relaxed state by radially compressing braided conductive member 28 with a sheath 33 (see FIG. 2). Upon retraction of sheath 33, braided conductive member 28 may radially expand a certain amount due to its filament winding structure, or due to elastic or spring elements attached to the filaments. In further embodiments, cable 22 may be used to urge braided conductive member 28 back into a longitudinally extended state by pushing on cap 24 or other distal attachment portion.

By retracting distal end 18 of braided conductive member 28 at least a certain distance in the proximal direction, a braided conductive member annular surface 30 may be formed in a plane that is substantially perpendicular to a distal end 26 of shaft portion 12, as illustrated in FIG. 4. Retracting distal end 18 further removes the projection of distal end 18 beyond annular surface 30, as illustrated in FIG. 5, which may allow annular surface 30 to be placed in contact with a cardiac wall or other cardiac tissue. If braided conductive member 28 is only partially inverted and distal end 18 projects beyond annular surface 30 in the distal direction, it may hinder efforts to contact cardiac tissue with the annular surface. In some embodiments, however, it may be desirable to maintain a portion of distal end 18 projecting from braided conductive member 28 so that braided conductive member 28 may be positioned relative to an ostium by inserting distal end 18 into the ostium. In some embodiments, the annular surface may be arranged such that it is contactable to a substantially flat area of tissue that has no ostia, even though an element may protrude distally from the annular surface. For example, a highly flexible element, such as a touch sensor, may protrude distally from the inverted braided conductive member and the annular surface would still be arranged such that it is contactable to a substantially flat area of tissue that has no ostia. The touch sensor may be a bend sensor that is positioned on the distal tip of the braided conductive member and protrudes slightly from the distally-facing surface when the braided conductive member is put into a deployed configuration. The bend sensor bends upon encountering a tissue wall and signals the controller that it has bent. The flexibility of the bend sensor allows the braided conductive member to contact the wall.

A "surface" need not be a continuous surface. For purposes herein, a "surface" of braided conductive member 28 refers to a plurality of interlaced conductive elements, such as filaments or wires, even though the interlaced elements may not fully occupy the space considered to be the surface. In some embodiments, wires or other conductive elements may be attached to or embedded in a flexible support material such that a solid surface is present.

The annular surface formed by inverting the braided conductive member 28 may have electrodes spaced around the entire annular surface. In other embodiments, electrodes may be positioned only on a portion or portions of the ring-shaped surface.

As illustrated in FIGS. 2-5, a sheath 33 may be provided. Sheath 33 serves to protect shaft portion 12 and braided conductive member 28 during manipulation through the patient's vasculature. In addition, sheath 33 may shield braided conductive member 28 from the patient's tissue in the event ablation energy is prematurely delivered to the braided conductive member 28.

Sheath 33 may be advanced and retracted over shaft portion 12 in any suitable manner. Control handle 14 may be used to effect the advancement or retraction of sheath 33. U.S. Pat. Nos. 5,383,852, 5,462,527, and 5,611,777, which are herein incorporated by reference in their entireties, illustrate examples of control handles that can control sheath 33. As described in these patents, control handle 14 may include a slide actuator which is axially displaceable relative to the handle. The slide actuator may be connected to sheath 33 to retract sheath 33 to expose braided conductive member 28 once the distal end of the catheter has been positioned within the heart or other target location.

Braided conductive member 28 may be shaped or biased such that when sheath 33 is retracted, braided conductive member 28 expands slightly in the radial direction. In other embodiments, braided conductive member 28 may maintain its longitudinally extended shape until cable 22 or other adjustment element is pulled in the proximal direction to longitudinally compress braided conductive member 28. In still other embodiments, braided conductive member 28 may maintain a radial size similar to its relaxed state radial size when distal tip 18 is moved proximally, or even when braided conductive member 28 is inverted.

Braided conductive member 28 is, in one embodiment of the invention, a plurality of interlaced, electrically conductive filaments 34. In some embodiments, braided conductive member 28 is a wire mesh. The filaments 34 are preferably formed of metallic elements having relatively small cross sectional diameters, such that the filaments are flexible and the braided conductive member can be expanded radially outwardly. In one embodiment, the filaments may be round in cross-section, having a dimension on the order of about 0.001-0.030 inches in diameter. Alternatively, the filaments may have flat sides in cross-section, with thicknesses on the order of about 0.001-0.030 inches, and widths on the order of about 0.001-0.030 inches. The filaments may be formed of nitinol-type wire or other shape memory alloys. Alternatively, the filaments may include non-metallic elements woven with metallic elements, with the non-metallic elements providing support to and/or separation of the metallic elements. A multiplicity of individual filaments 34 may be provided in braided conductive member 28, for example three hundred or more filaments. Instead of a multiplicity or plurality of filaments, a smaller number of filaments, or even only one continuous filament may be arranged to form braided conductive member 28. For purposes herein, the terms "filaments" or "plurality of filaments" may refer to one continuous filament that is interlaced with itself to form a braided conductive member.

Each of the filaments 34 may be electrically isolated from each other by an insulation coating. This insulation coating may be, for example, a polyamide type material. In one manner of forming an electrode, a portion of the insulation on the filaments forming an outer circumferential surface of braided conductive member 28 is removed. This arrangement allows each of the filaments 34 to form an isolated electrode, not in electrical contact with any other filament, that may be used for mapping and ablation. In some embodiments, an electrode may contact a coated section of another filament. Alternatively, specific electrodes may be permitted to contact each other to form a preselected grouping. Methods of removing insulation from filaments 34 are disclosed in PCT Publication No. WO 02/087437, which is herein incorporated by reference in its entirety. The insulation may also be removed in a preferential manner so that a particular portion of the circumferential surface of a filament 34 is exposed. In this manner, when braided conductive member 28 is radially expanded, the stripped portions of filaments may preferentially face an intended direction of mapping or ablation.

Further, in some embodiments some of filaments 34 may be used for mapping or electrical measurement, while others of filaments 34 may be used for ablation. The mapping and ablation filaments may be activated independently or may be activated concurrently. One application of dedicating some filaments for mapping and others for ablation is using a single braided conductive member 28 to both form a lesion and measure the quality of the lesion. Such an arrangement can avoid a change of catheters during a medical procedure. Temperature sensors (not shown) also may be included on catheter shaft 12 or braided conductive member 28.

A wire (not shown) may run from each of the filaments 34 to connector portion 16 via conductors (not shown). A multiplexer or switch box may be connected to the conductors so that each filament 34 may be controlled individually. This function may be incorporated into controller 8. In some embodiments, a number of filaments 34 may be grouped together for mapping and ablation. Alternatively, each individual filament 34 may be used as a separate mapping channel for mapping individual electrical activity at a single point. Using a switch box or multiplexer to configure the signals being received by filaments 34 or ablation energy sent to filaments 34 results in a large number of possible combinations of filaments for detecting electrical activity during mapping procedures and for applying energy during an ablation procedure.

Catheter 10 may also have a reference electrode (not shown) mounted on shaft 12 so that the reference electrode is located outside the heart during unipolar mapping operations.

Individual control of the electrical signals received from filaments 34 allows catheter 10 to be used for bipolar (differential or between filament) type mapping as well as unipolar (one filament with respect to a reference electrode) type mapping.

Catheter 10 may be a steerable device, in some embodiments, in that the distal end 26 may be deflected by an actuator contained within control handle 14. Control handle 14 may include a rotatable thumb wheel which can be used by a user to deflect distal end 26 of the catheter. The thumb wheel (or any other suitable actuating device) is connected to one or more pull wires (not shown) which extend through shaft portion 12 and connect to distal end 18 of the catheter at an off-axis location, whereby tension applied to one or more of the pull wires causes the distal portion of the catheter to curve in a predetermined direction or directions. U.S. Pat. Nos. 5,383,852, 5,462,527, and 5,611,777 illustrate various embodiments of control handle 14 that may be used for steering catheter 10.

Figure 6:
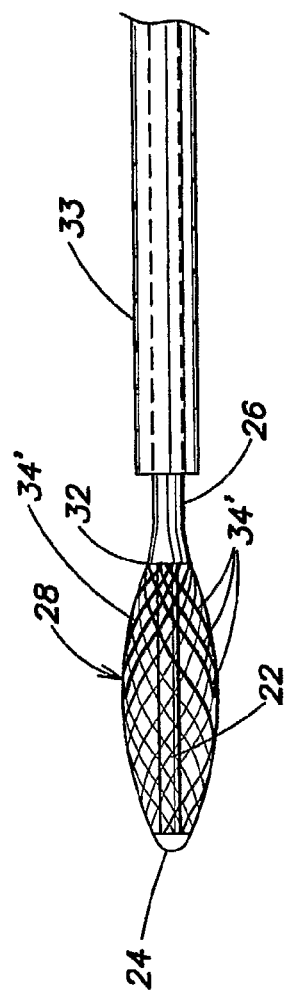
FIG. 6 illustrates a braided conductive member including support elements that may be used in one embodiment of the invention.
Figure 7:
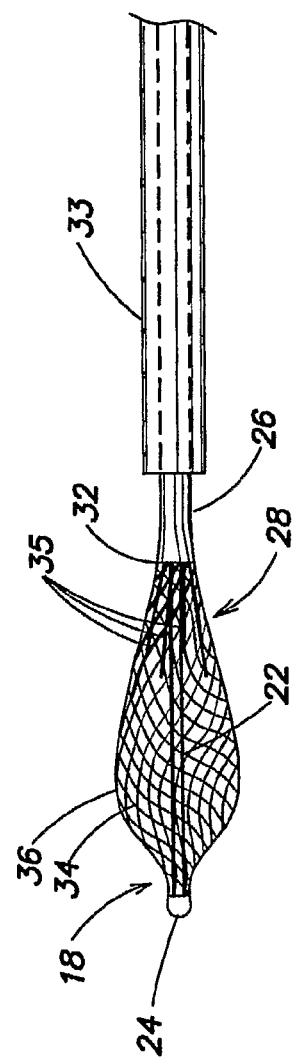
FIG. 7 illustrates a braided conductive member that may be used in one embodiment of the invention.

In some embodiments, a proximal portion of braided conductive member 28 includes support elements to aid in maintaining the shape and/or structural integrity of portions of braided conductive member 28 when distal end 18 is moved in the proximal direction. For example, support elements may include support filaments 34' that are stronger, thicker or more rigid at their proximal ends than at their distal ends, as illustrated in FIG. 6. In other embodiments, splines 35 or other non-filament elements may be included, such as by interlacing support elements among filaments 34, as illustrated in FIG. 7. In still further embodiments, support elements which are not interlaced with filaments 34 may be included. In some embodiments, support elements attach to a proximal anchoring element 32 at a first end and to cap 24 or filaments 34 at a second end.

Referring to FIG. 7, an embodiment of the invention having a longitudinally asymmetrically shaped braided conductive member 28 is illustrated. In this embodiment, a maximum diameter 36 of braided conductive member 28 is located closer to distal end 18 than to proximal anchoring element 32. In one embodiment, maximum diameter 36 is longitudinally located more than two-thirds of the way from the proximal anchoring location to the distal attachment location. As cable 22 is drawn in the proximal direction to move cap 24, splines 35 support the more proximal region of braided conductive member 28.

Figure 8:
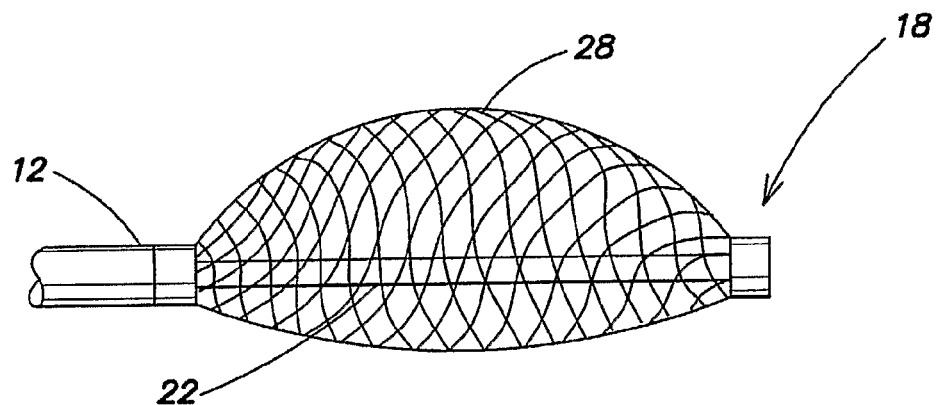
FIG. 8 illustrates an alternate embodiment of the braided conductive member that may be used on one embodiment of the invention.

Reference is now made to FIG. 8 which illustrates another shape of braided conductive member 28. As described above regarding various embodiments of the invention, braided conductive member 28 may be generally radially symmetrical. However, certain anatomical structures may have complex three-dimensional shapes that are not easily approximated by a geometrically symmetrical mapping or ablation structure. To successfully contact these types of anatomical structures, braided conductive member 28 can be "preformed" to a close approximation of that anatomy, and yet still be flexible enough to adapt to variations found in specific patients. Alternatively, braided conductive member 28 can be of sufficient strength (as by choice of materials, configuration, etc.) to force the tissue to conform to variations found in specific patients. For example, FIG. 8 illustrates braided conductive member 28 disposed about shaft 12 in an off-center or non-concentric manner such that braided conductive member 28 is radially asymmetrically-shaped. In addition, braided conductive member 28 may also be constructed so that the annular surface of the braided conductive member in its expanded configuration is a non-circular surface so as to improve tissue contact. FIG. 8 illustrates an example of this type of configuration where the braided conductive member 28 is constructed and arranged to be non-concentric with respect to a longitudinal axis of braided conductive member 28 and also, in its expanded configuration, to have an asymmetric shape. In some embodiments, the asymmetric expanded configurations and the eccentricity of braided conductive member 28 with respect to the longitudinal axis can be produced by providing additional structural supports in braided conductive member 28, for example, by adding nitinol wire, ribbon wire, splines, and so on. Other suitable methods of creating the eccentric and/or asymmetric shape include: varying the winding pitch; varying individual filament size and/or placement; deforming selective filaments in braided conductive member 28; and any other suitable method known to those skilled in the art.

An asymmetrically-shaped braided conductive member may allow for the formation of a ring-shaped surface that is disposed at an angle to general longitudinal direction of the braided member and/or the distal end of the catheter. The angled surface may permit better contact with certain tissue areas. In still other embodiments, inverting the braided conductive member may form a non-planar surface. For example, differing filament diameters may allow for the formation of a ring-shaped surface which includes a section that is substantially perpendicular to the catheter and a section that is disposed at an angle to the catheter. The angle of the surface relative to the catheter may change continuously across the surface in still other embodiments.

In some embodiments of the present invention, catheter 10 may be coated with a number of coatings that enhance the operating properties of braided conductive member 28. The coatings may be applied by any of a number of techniques and the coatings may include a wide range of polymers and other materials.

Braided conductive member 28 may be coated to reduce its coefficient of friction, thus reducing the possibility of thrombi adhesion to the braided conductive member as well as the possibility of vascular or atrial damage. These coatings can be combined with insulation (if present) on the filaments that make up braided conductive member 28. These coatings may be included in the insulation itself, or the coatings may be applied over the insulation layer.

Braided conductive member 28 also may be coated to increase or decrease its thermal conduction, which can improve the safety or efficacy of the braided conductive member 28. This change in thermal conduction may be achieved by incorporating thermally conductive elements or thermally insulating elements into the electrical insulation of the filaments that make up braided conductive member 28, or by adding a coating to the assembly. Polymer mixing, IBAD, or similar technology could be used to add Ag, Pt, Pd, Au, Ir, Cobalt, and others into the insulation or to coat braided conductive member 28.

In some embodiments, radioopaque coatings or markers may be used to provide a reference point for orientation of braided conductive member 28 when viewed during fluoroscopic imaging. The materials that provide radiopacity include, for example, Au, Pt, Ir, and others known to those skilled in the art. These materials may be incorporated and used as coatings as described above.

Antithrombogenic coatings, such as heparin and BH, can also be applied to braided conductive member 28 to reduce thrombogenicity to prevent blood aggregation on braided conductive member 28. These coatings can be applied by dipping or spraying, for example.

As noted above, the filament 34 of braided conductive member 28 may be constructed of metal wire materials. These materials may be, for example, MP35N, nitinol, or stainless steel. Filaments 34 may also be composites of these materials in combination with a core of another material such as silver or platinum. The combination of a highly conductive electrical core material with another material forming the shell of the wire allows the mechanical properties of the shell material to be combined with the electrical conductivity of the core material to achieve better and/or selectable performance. The choice and percentage of core material used in combination with the choice and percentage of shell material used can be selected based on the desired performance characteristics and mechanical/electrical properties desired for a particular application.

There may be times during ablation or mapping procedures when catheter 10 passes through difficult or tortuous vasculature. During these times, it may be helpful to have a guiding sheath (not shown) through which to pass catheter 10 so as to allow easier passage through the patient's vasculature.

Irrigation

Figure 9:
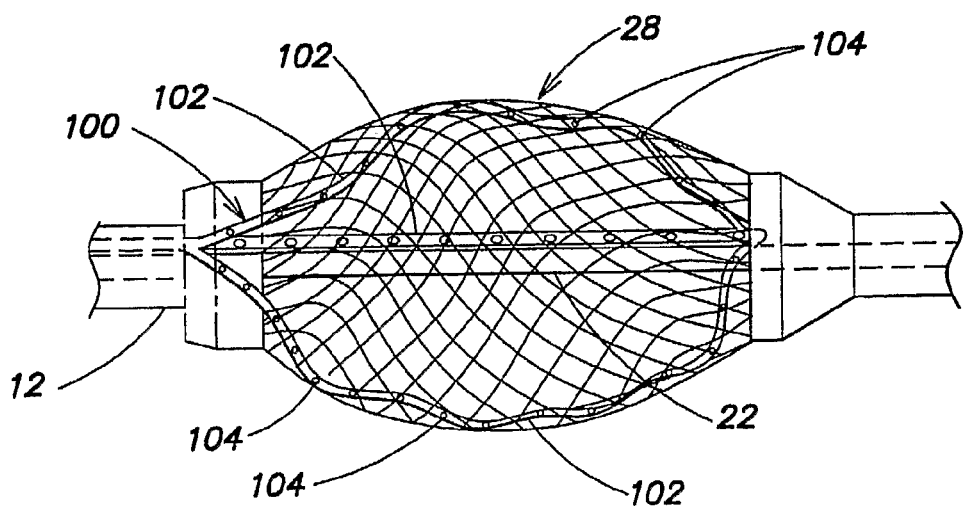
FIG. 9 illustrates the use of irrigation according to one embodiment of the invention.

It is known that for a given electrode side and tissue contact area, the size of a lesion created by radiofrequency (RF) energy is a function of the RF power level and the exposure time. At higher powers, however, the exposure time can be limited by an increase in impedance that occurs when the temperature at the electrode-tissue interface approaches at 100° C. One way of maintaining the temperature less than or equal to this limit is to irrigate the ablation electrode with saline to provide convective cooling so as to control the electrode-tissue interface temperature and thereby prevent an increase in impedance. Accordingly, irrigation of braided conductive member 28 and the tissue site at which a lesion is to be created can be provided in the present invention. FIG. 9 illustrates the use of an irrigation manifold within braided conductive member 28. An irrigation manifold 100 is disposed along shaft 12 inside braided conductive member 28. Irrigation manifold 100 may be one or more polyimide tubes. Within braided conductive member 28, the irrigation manifold splits into a number of smaller tubes 102 that are woven into braided conductive member 28 along a respective filament 34. A series of holes 104 may be provided in each of the tubes 102. These holes can be oriented in any number of ways to target a specific site or portion of braided conductive member 28 for irrigation. Irrigation manifold 100 runs through catheter shaft 12 and may be connected to an irrigation delivery device outside the patient used to inject an irrigation fluid, such as saline, for example, such as during an ablation procedure.

The irrigation system can also be used to deliver a contrast fluid for verifying location or changes in vessel diameter. For example, a contrast medium may be perfused prior to ablation and then after an ablation procedure to verify that there have been no changes in the blood vessel diameter. The contrast medium can also be used during mapping procedures to verify placement of braided conductive member 28. In either ablation or mapping procedures, antithrombogenic fluids, such as heparin can also be perfused to reduce thrombogenicity.

Figure 10:
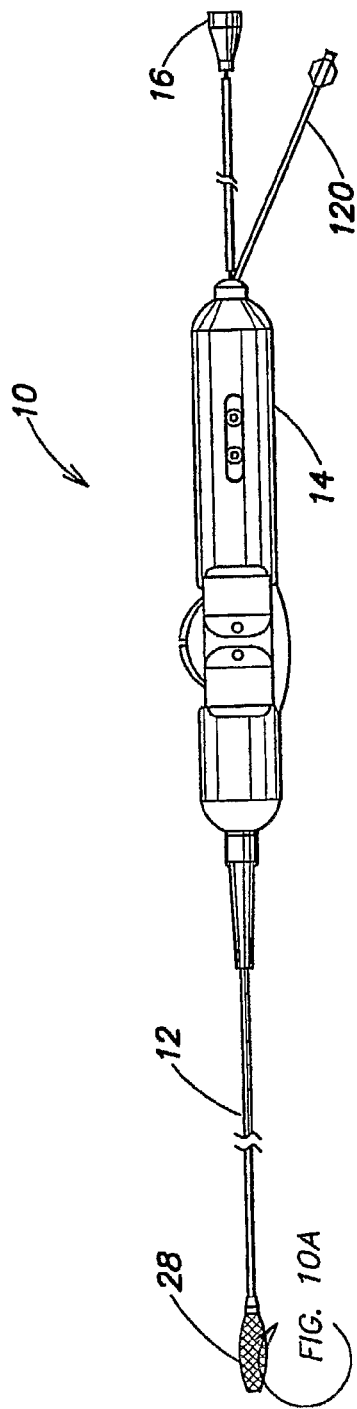
FIG. 10 illustrates the use of irrigation according to another embodiment of the invention.
Figure 10A:
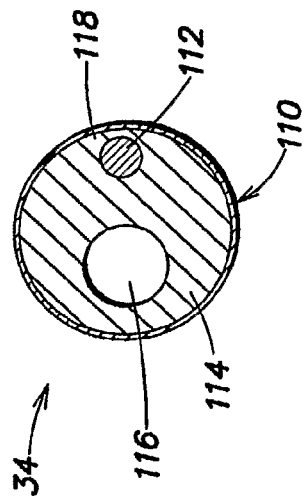
FIG. 10A is an enlarged cross-sectional view of a filament used in the braided conductive member illustrated in FIG. 10.

FIG. 10 illustrates another way of providing perfusion/irrigation in catheter 10. As illustrated in FIG. 10, the filaments 34 that comprise braided conductive member 28 may be composed of a composite wire 110. The composite wire 110 includes a lumen 114 containing an electrically conductive wire 112 that is used for delivering ablation energy in an ablation procedure or for detecting electrical activity during a mapping procedure. Composite wire 110 also contains a perfusion lumen 116. Perfusion lumen 116 is used to deliver irrigation fluid or a contrast fluid as described in connection with FIG. 9. Once braided conductive member 28 has been constructed with composite wire 110, the insulation 118 surrounding wire filament 112 can be stripped away to form an electrode surface. Holes can then be provided in perfusion lumen 116 to then allow perfusion at targeted sites along the electrode surface. As with the embodiment illustrated in FIG. 9, the perfusion lumens can be connected together to form a manifold which manifold can then be connected to, for example, perfusion tube 120 and connected to a fluid delivery device.

Methods of Use

Figure 11:
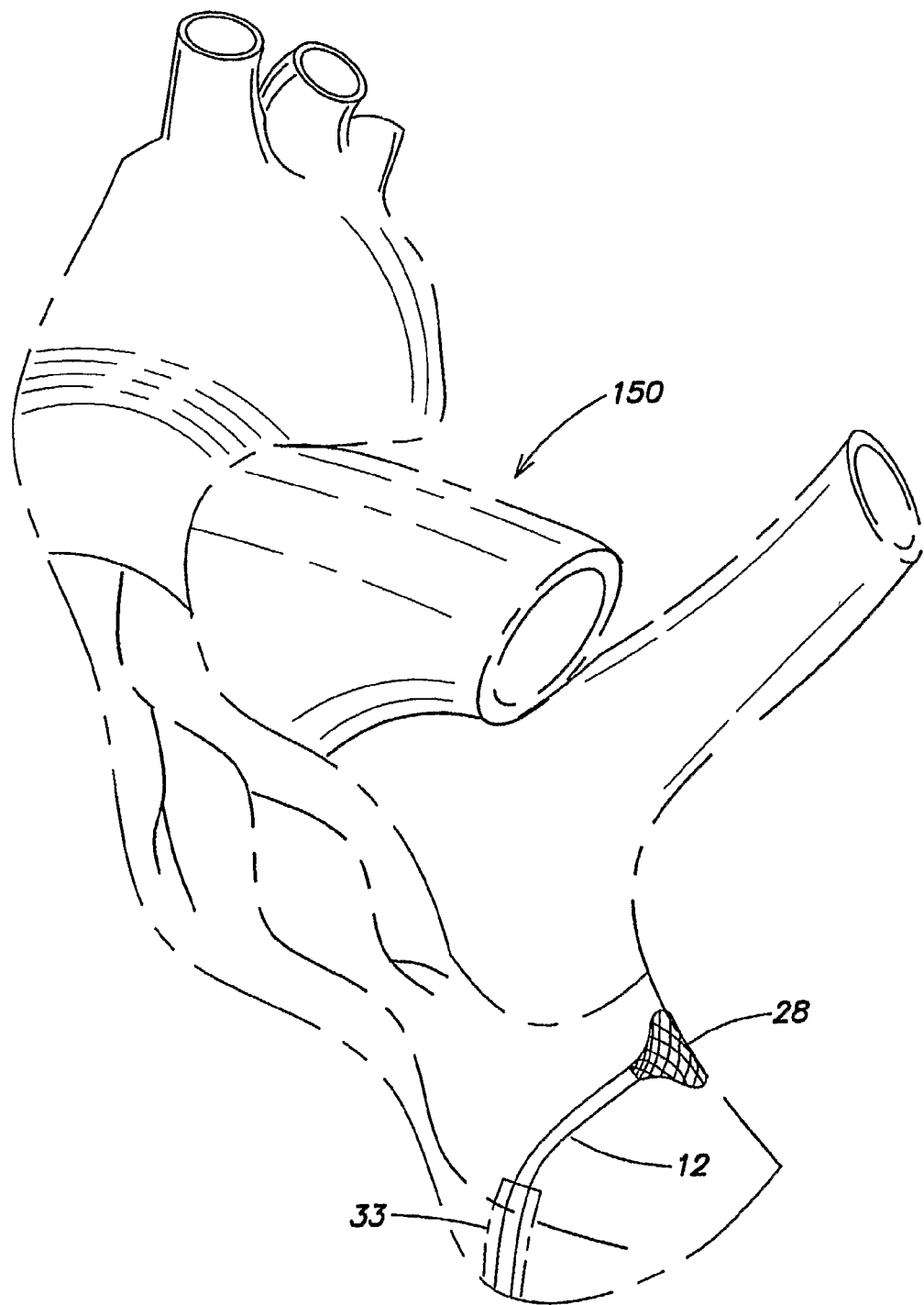
FIG. 11 illustrates one embodiment of a method of using a catheter and the braided conductive member.

Reference is now made to FIG. 11 which illustrates how a catheter according to certain embodiments of the present invention may be used in endocardial applications.

In an endocardial procedure, shaft portion 12 is introduced into a patient's heart 150. Appropriate imaging guidance (direct visual assessment, camera port, fluoroscopy, echocardiographic, magnetic resonance, etc.) can be used. FIG. 11 in particular illustrates shaft portion 12 being placed in the left atrium of the patient's heart. Once shaft portion 12 reaches the patient's left atrium, sheath 33 may be retracted and braided conductive member 28 may be inverted to its deployed state, where, in the illustrated embodiment, braided conductive member 28 forms a cone-type shape including a distally-facing, ring-shaped surface. External pressure may be applied along shaft portion 12 to achieve the desired level of contact between braided conductive member 28 and the cardiac tissue. In one embodiment, mapping of electrical impulses may be achieved with braided conductive member 28. In another embodiment, energy is applied to the cardiac tissue in contact with braided conductive member 28 to create an annular lesion. The energy used may be RF (radiofrequency), DC, microwave, ultrasonic, cryothermal, optical, etc.

In some embodiments, the braided conductive member may be configured such that it forms a distally-facing, ring-shaped surface before the braided conductive member is introduced to the heart.

Figure 13:
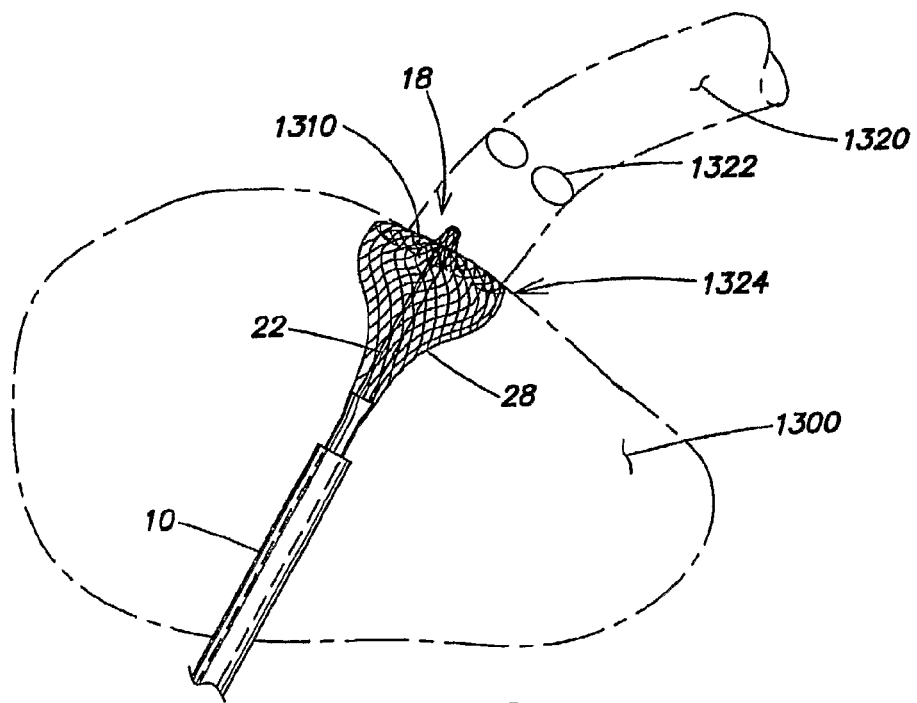
FIG. 13 is a sketch illustrating a method of treating arrhythmia.

Braided conductive member 28 may be used for mapping and/or ablation in other chambers of the heart. FIG. 13 shows catheter 10 with braided conductive member 28 used in a method of treating ventricular tachycardia. In this illustrated embodiment, the tachycardia is emanating from the outflow track 1320 of ventricle 1300, which may represent either a right or left ventricle. In the illustrated method, the braided conductive member 28 is placed in a partially inverted position such as illustrated in FIG. 4. The partially inverted configuration leaves a distal end 18 extending beyond a distally facing surface 1310. In this embodiment, distal end 18 extends partially into the outflow track 1320 and may aid in positioning braided conductive member 28 relative to outflow tract 1320.

Distal end 18 forms a proboscis that may be used in cannulating a blood vessel such as outflow tract 1320. Where desired, catheter 10 may be formed with an extension forming a longer proboscis that may extend further into a blood vessel such as outflow tract 1320. The proboscis may, for example, be long enough to extend beyond pulmonary valve 1322. Providing a catheter with a longer proboscis may aid in positioning braided conductive member 28 relative to the ostium 1324 of outflow track 1320. Positioning provided by a proboscis may aid in assuring a stable contact between surface 1310 and the endocardium so that reliable mapping and ablation may be achieved.

Figure 12:
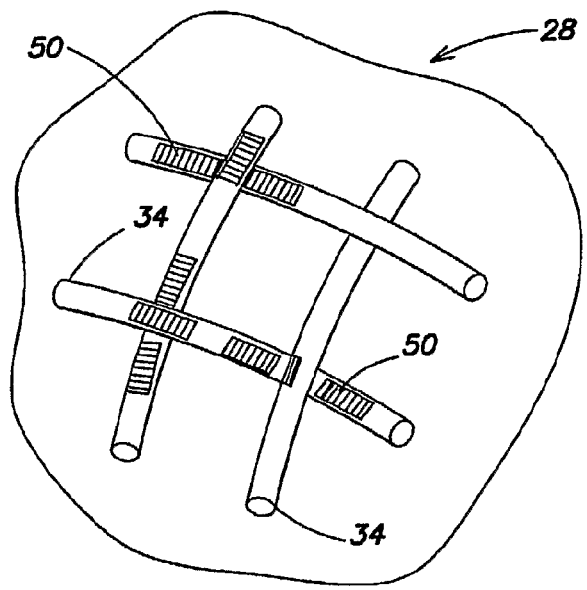
FIG. 12 is a sketch illustrating electrically active sites on a surface of a catheter.

FIG. 12 shows an enlarged view of a portion of surface 1310. In this example, surface 1310 is defined by filaments 34 of braided conductive member 28. Braided conductive member 28 serves as a substrate for holding multiple electrically active sites 50. In the illustrated embodiment, electrically active sites are formed by selectively removing insulation from filaments 34. The insulation may be removed in any suitable manner, such as by milling or laser ablation techniques.

In the illustrated embodiments, the electrically active sites 50 face outwards from the center of braided conductive member 28. As the surfaces of braided conductive member 28 comes in contact with tissue, one or more of the electrically active sites will be in electrical connection with that tissue. Impedance measurement techniques as known in the art may be used to detect which electrically active sites make contact with tissue.

Because filaments 34 are electrically conducting, a conducting path between the electrically active sites 50 and controller 8 is formed through cable 6. Controller 8 may therefore send or receive signals to the electrically active sites 50. In some embodiments, conductive filaments are electrically insulated except where electrically active sites 50 are formed. In this way, electrically active sites on separate ones of the filaments 34 may be separately accessed by controller 8. In other embodiments, one or more of the filaments 34 may be in electrical contact with each other. In this embodiment, exposed regions on multiple filaments may collectively form an electrically active site.

Separate access to the electrically active sites 50 allows controller 8 to configure braided conductive mesh 28 to send or receive electrical signals in a configurable pattern by selecting specific ones of the electrically active sites 50 to access simultaneously. For example, the surface 1310 illustrated in FIG. 13 may be divided into quadrants surrounding ostium 1324. The electrically active sites in each quadrant may be separately accessed for mapping purposes to determine which quadrant contains the focus of a tachycardia. Access sites in quadrants is just one example of a configuration that may be used. Controller 8 may access the electrically active sites 50 in any combination or may access electrically active sites individually. In this way, a focus of a tachycardia may be detected with very high resolution. In one embodiment, thirty-six electrically active sites are disposed on braided conductive member 28. However, any number of electrically active sites may be used.

Providing a stable substrate for the electrically active sites further increases the resolution with which sites for mapping or ablation are selected. Braided conductive member 28 is desirable for use in mapping and ablation procedures because it provides a substrate that holds the electrically active sites in a stable fashion during a mapping or ablation procedure.

In use, catheter 10 may be positioned near the suspected focus of a tachycardia. It may be stably positioned, such as by cannulating a blood vessel with a proboscis extending from catheter 10 or by pressing a surface 1310 against a wall of the heart. Braided conductive member 28 may be configured as desired such as in an inverted or partially inverted configuration as described above. Once positioned, controller 8 may receive signals through conductive filaments 34 from selected electrically active sites 50 for passive mapping. Alternatively, controller 8 may send stimulus signals through the conductive filaments 34 to selected ones of the electrically active sites 50 for pace mapping in connection with a surface ECG, as is know in the art. If a focus on the tachycardia is detected, controller 8 may send RF signals through the conductive filaments 34 to selected ones of the electrically active sites 50 for ablation. In this way, a single catheter may be used for passive mapping, pace mapping and/or ablation.

Controller 8 may send RF energy for ablation to all of the electrically active sites 50 on surface 1310, thereby providing ablation energy substantially around the parameter of ostium 1324. When operated in this configuration, ablation may cause an annular lesion. However, where an annular lesion is not required to either ablate the focus or block re-entry circuits, the ablation energy may be provided to groups of electrically active sites to create different ablation patterns. For example, ablation energy may be provided to a single electrically active site 50 or a small number of electrically active sites in close proximity to ablate tissue at one point. Alternatively, a group of electrically active sites positioned in a line or arc on surface 1310 may be formed. When ablation energy is applied to this group, a lesion in the shape of a line or arc may be formed.

Figure 14A:
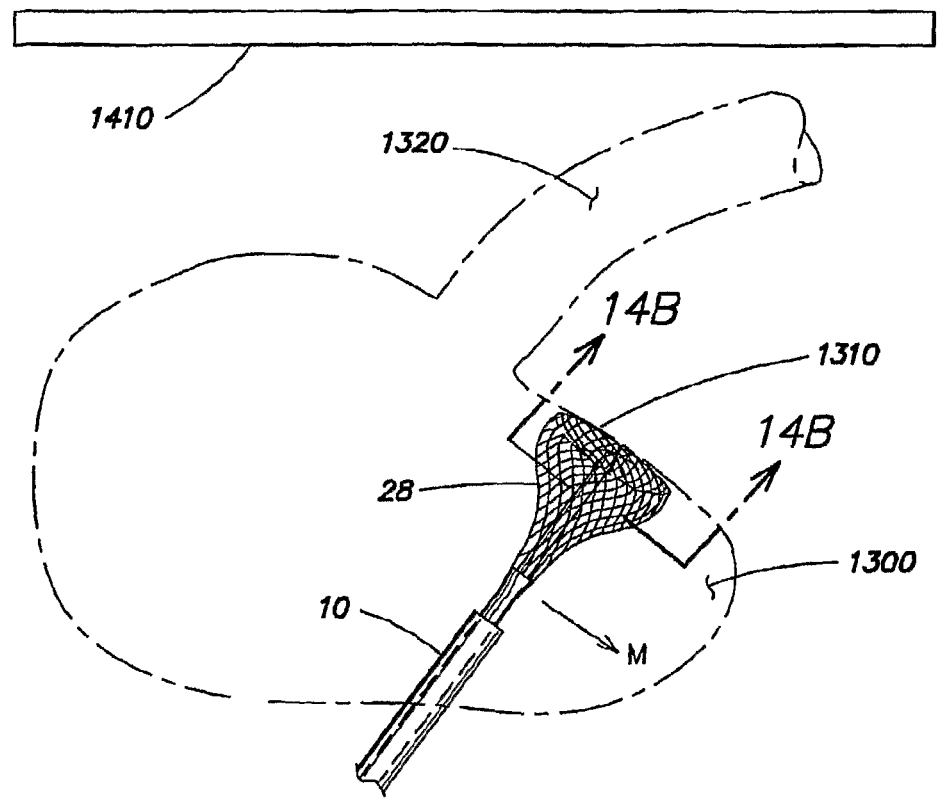
FIG. 14A is a sketch illustrating a method of treating arrhythmia.
Figure 14B:
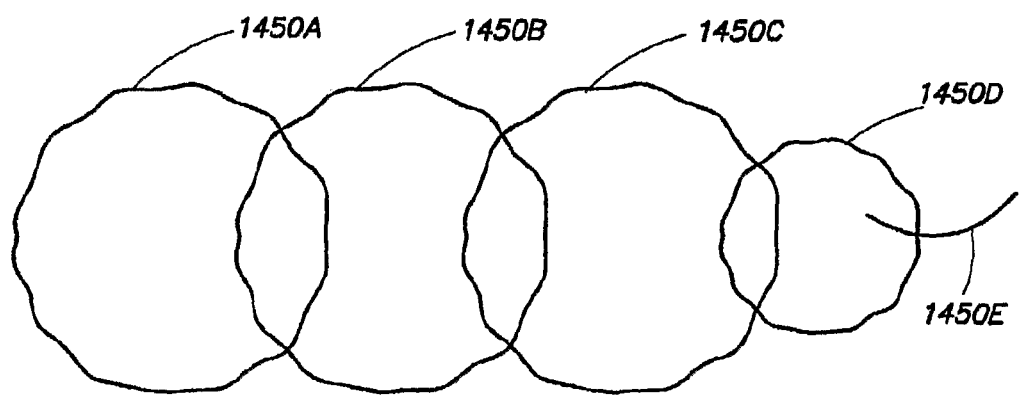
FIG. 14B is a sketch illustrating a pattern of lesions formed in accordance with the method of FIG. 14A.
Figure 14C:
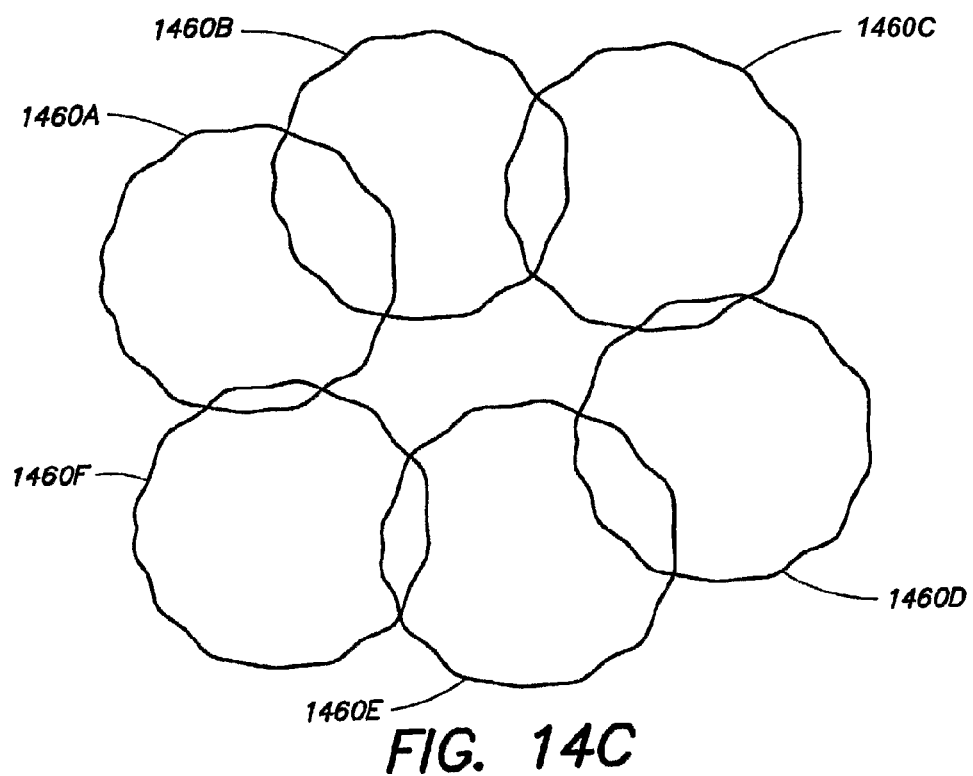
FIG. 14C is a sketch illustrating an alternative pattern of lesions formed in accordance with the method of FIG. 14A.

FIGS. 14A, 14B, and 14C illustrate use of braided conductive member 28 in an alternative process for detecting and treating arrhythmias. In this embodiment, braided conductive member 28 has been introduced into a chamber of a heart, such as a ventricle 1300. In this embodiment, braided conductive member 28 has been configured as shown in FIG. 5 to provide a relatively planar surface without a distal end 18 forming a proboscis as illustrated in FIG. 13. Surface 1310 may therefore be pressed against the wall of a chamber of the heart. Braided conductive member 28 is flexible and may therefore conform to the shape of the surface, creating good electrical and mechanical contact between the electrically active sites 50 and the surface of the heart. The position for contacting braided conductive matter 28 to the heart may be selected based on a suspected location of a focus of an arrhythmia. As illustrated by FIG. 14A, the selected site need not be limited by placement relative to outflow tract 1320 or other blood vessel.

Once braided conductive member 28 is positioned, controller 8 may send and/or receive signals from the electrically active sites for mapping and/or ablation. It is not necessary, however, that braided conductive member 28 be used for both mapping and ablation. It may, for example, be desirable to use an ablation catheter of a different shape for ablating tissue once foci of an arrhythmia are identified. To facilitate use of multiple catheters, a navigation system 1410 as is known in the art may be employed in connection with a mapping and/or ablation process. A navigation system may create a set of transverse electric or magnetic fields with a gradient. A sensor positioned within the electric or magnetic fields that is sensitive to the strength of the field in each of the transverse directions may be used to identify the position of a catheter. Such a navigation system would allow, for example, braided conductive mesh 28 to be used for mapping of cardiac arrhythmia. Once a focus of the arrhythmia is detected, the position of the focus may be related to positions as determined by the navigation system. An additional catheter may be inserted for ablation at the desired location as indicated by the navigation system, with or without removing braided conductive member 28.

However, the braided conductive mesh may be used for ablation and may be configured to provide a wide range of ablation patterns. FIG. 14B shows the surface of ventricle 1300 as seen in the direction indicated by the line B-B in FIG. 14A. FIG. 14B illustrates an ablation pattern that may be created by repositioning catheter 10, and therefore braided conductive member 28, and then applying ablation energy with braided conductive member 28 in different positions. For example, lesions 1450A, 1450B, and 1450C are substantially annular lesions. Such lesions may be formed by providing ablation energy to all of the electrically active sites on surface 1310. Each of the successive lesions may be formed by moving catheter 10 in the direction M between each application of ablation energy.

In the example of FIG. 14B, lesion 1450D is also formed by moving catheter 10 in the direction M. In this example, lesion 1450D is also annular, but with a radius smaller than lesions 1450A, 1450B, and 1450C. A smaller lesion may be formed by manipulating braided conductive member 28 to present a smaller surface area 1310 against the wall of the heart. The surface area may be changed, for example, by manipulation of cable 22 as described above.

FIG. 14B also illustrates another type of flexibility provided by braided conductive member 28. Lesion 1450E is shown to be in the shape of a line or segment. Such a lesion may be formed by providing ablation energy to only a subset of the electrically active sites on surface 1310. As demonstrated by FIG. 14B, the shape and size of a lesion formed by ablation using braided conductive member 28 may be controlled using multiple parameters including the position of catheter 10, the shape of braided conductive member 28 and the pattern of electrically active sites used in driving ablation energy.

Figure 14D:
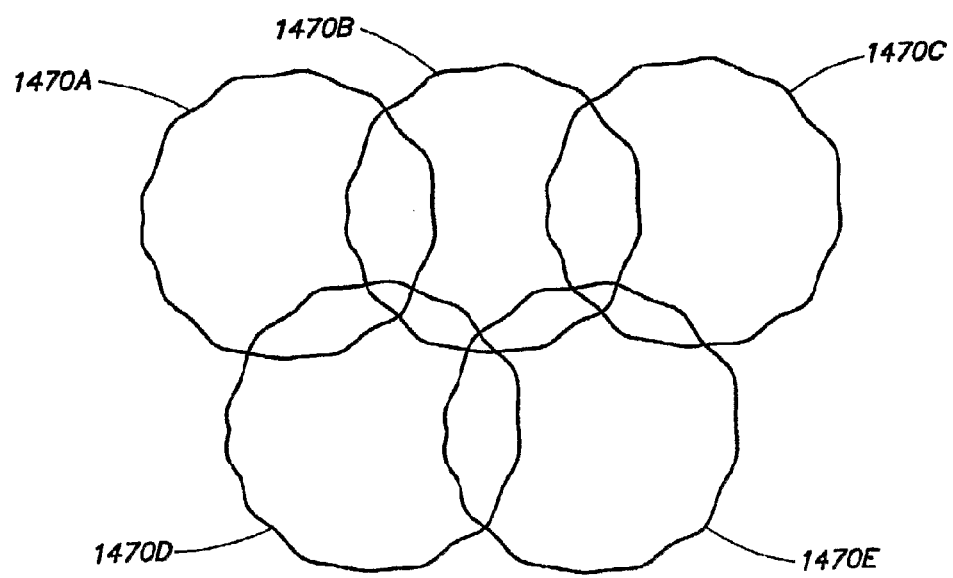
FIG. 14D is a sketch illustrating an alternative pattern of lesions formed in accordance with the method of FIG. 14A.

FIG. 14C illustrates a further example of an ablation pattern that may be formed. Catheter 10 may be moved in any desired direction to reposition braided conductive member 28. In the example shown in FIG. 14C, catheter 10 has been moved in a circular pattern to create a circular pattern of overlapping annular lesions 1460A, 1460B, 1460C, 1406D, 1460E, and 1460F. Other lesion patterns are possible. For example, multiple annular lesions may be overlapped in a pattern similar to the olympic rings as shown in FIG. 14D. In FIG. 14D lesions 1470A, 1470B, 1470C, 1470D, and 1470E are formed by successive applications of ablation energy with braided conductive member 28 in different positions.

The examples of FIGS. 14B, 14C, and 14D illustrate the flexibility of patterning lesions formed by ablation with braided conductive member 28. This flexibility makes such a catheter suitable for detecting and treating arrhythmias, such as those occurring in the ventricles. The braided conductive member may be fully deployed to create a relatively large surface, such as 1310, for mapping. For example, surface 1310 may have a diameter in excess of 15 mm and in some embodiments has a diameter of between about 25 and 30 mm. Mapping over such a large and stable area increases the success rate for accurately localizing foci. Also, mapping over such a wide area can speed up the entire procedure, reducing stress on patient. Ablation energy may also be provided in configurable patterns across this relatively large surface.

Furthermore, the fact that braided conductive member 38 does not create a continuous surface can provide benefits in cooling during an ablation procedure. Cooling may be provided by the natural flow of blood in the heart or may be enhanced through irrigation as described above. Providing cooling allows for higher energies or longer ablation times, therefore making the braided conductive member 28 well suited for ablating arrhythmic foci in the ventricles, which tend to be relatively deep foci. Such a design may be particularly advantageous for treating ventricular tachycardia, particularly those with foci in the region of the ventricular outflow tract where it has traditionally be difficult to stably position a mapping catheter for accurate localization of foci and where it has also been traditionally difficult to ablate a broad and deep region necessary to destroy the foci or block re-entry. Such a design also may be particularly advantageous in treating idiopathic ventricular tachycardia that has been traditionally difficult to treat.

However, the method and apparatus described herein are not limited for use in connection with detection and treatment of ventricular tachycardia.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of treating an arrhythmia in a heart, comprising the acts of:
   (a) introducing a substrate into a chamber of the heart;
   (b) placing the substrate in contact with the heart while in a first configuration;
   (c) performing at least one of mapping and pacing by transmitting electrical signals between the substrate and a control location;
   (d) reconfiguring the substrate into a second configuration, different than the first configuration;
   (e) forming a first annular lesion that encircles a first region by ablating a region of the heart adjacent the substrate;
   (f) repositioning the substrate; and
   (g) forming a second annular lesion that encircles at least a portion of the first region encircled by the first annular lesion.

2. The method of claim 1, additionally comprising the acts of:
   (h) repositioning the substrate;
   (i) forming a third annular lesion at least partially overlapping the first annular lesion and the second annular lesion.

3. The method of claim 2, wherein less than half of area within the third annular lesion is common to each of the first and second annular lesions.

4. The method of claim 1, wherein the act (a) comprises introducing a braided conductive member into a chamber of the heart.

5. The method of claim 1, wherein the act (d) comprises reconfiguring the substrate into a second configuration, having a smaller surface area than the first configuration.

6. The method of claim 5 wherein:
   the act (a) comprises introducing a braided conductive member in a chamber of the heart; and
   the act (d) comprises changing a spacing between a proximal end and a distal end of the braided conductive member.

7. The method of claim 1, wherein:
   the substrate while in the first configuration contacts the heart over a first area; and the act (e) comprises ablating a region of the heart adjacent the substrate that is smaller than the first area.

8. The method of claim 7, wherein:
the substrate comprises a braided conductive member having a plurality of electrically active sites; and
the act (e) comprises providing ablation energy to a subset of the plurality of electrically active sites.

9. The method of claim 1, wherein the act (d) of reconfiguring comprises moving the center of the substrate away from the heart.

10. The method of claim 1, wherein the substrate has a proboscis extending therefrom and the act (b) comprises cannulating a blood vessel connected to the heart with the proboscis.

11. The method of claim 1, wherein:
the arrhythmia is an idiopathic ventricular tachycardia;
the chamber of the heart is a ventricle; and
the act (e) additionally comprises passing a fluid through the substrate.

12. The method of claim 1, wherein less than half of area within the second annular lesion is common to the first annular lesion.

13. The method of claim 1, wherein the first and second annular lesions respectively encircle first and second regions of a heart wall, and wherein neither of the first and second regions of the heart wall comprises an ostium of a blood vessel.

14. A method of using a catheter comprising a substrate, comprising the acts of:
(a) introducing the substrate into a ventricle of the heart, the substrate comprising a distal end;
(b) configuring the substrate in a first configuration wherein the distal end of the substrate forms a proboscis extending from the substrate;
(c) with the substrate in the first configuration and the proboscis cannulating a blood vessel connected to the heart, ablating a first lesion on a wall of the ventricle, the first lesion at least partially encircling a first region of the wall that includes an ostium of the blood vessel;
(d) configuring the substrate in a second configuration wherein the substrate is inverted such that an annular surface of the substrate extends beyond the distal end;
(e) with the substrate in the second configuration, ablating a second lesion on the wall of the ventricle, the second lesion encircling a second region of the wall that does not include any blood vessel ostia.

15. The method of claim 14, wherein the first lesion fully encircles the first region.

* * * * *